(12) United States Patent  
Järvikivi et al.

(10) Patent No.: US 9,310,324 B2  
(45) Date of Patent: Apr. 12, 2016

(54) X-RAY FLUORESCENCE ANALYZER WITH SAFETY FEATURES

(71) Applicant: Oxford Instruments Analytical Oy, Espoo (FI)

(72) Inventors: Mikko Järvikivi, Espoo (FI); Jarmo Leino, Lohja (FI)

(73) Assignee: Oxford Instruments Analytical Oy, Espoo (FI)

( * ) Notice: Subject to any disclaimer, the term of this patent is extended or adjusted under 35 U.S.C. 154(b) by 92 days.

(21) Appl. No.: 14/034,607

(22) Filed: Sep. 24, 2013

(65) Prior Publication Data

US 2015/0085976 A1  Mar. 26, 2015

(51) Int. Cl.  
  *G01N 23/00* (2006.01)  
  *G01N 23/223* (2006.01)
(52) U.S. Cl.  
  CPC ........ *G01N 23/223* (2013.01); *G01N 2223/301* (2013.01)
(58) Field of Classification Search  
  USPC .......................................................... 378/44  
  See application file for complete search history.

(56) References Cited

U.S. PATENT DOCUMENTS

| 4,686,694 | A  * | 8/1987  | Berry ................... G01N 23/223 250/498.1 |
| 6,486,573 | B2 * | 11/2002 | Yagi ..................... G01N 23/223 307/328 |
| 7,916,834 | B2 * | 3/2011  | Piorek .................. G01N 23/223 378/102 |
| 2005/0023479 | A1* | 2/2005 | Grodzins ................. G01T 3/06 250/390.11 |
| 2005/0127300 | A1 | 6/2005 | Bordynuik |
| 2005/0226373 | A1 | 10/2005 | Trombka |
| 2009/0220045 | A1 | 9/2009 | Grodzins |
| 2010/0080351 | A1 | 4/2010 | Hession-Kunz et al. |
| 2013/0094627 | A1 | 4/2013 | Lalleman et al. |

FOREIGN PATENT DOCUMENTS

DE    19704708    8/1998

* cited by examiner

*Primary Examiner* — Phillip A Johnston  
(74) *Attorney, Agent, or Firm* — Harrington & Smith

(57) ABSTRACT

A portable X-ray fluorescence analyzer comprises a detector of ionizing radiation that is configured to detect radiation from spontaneous radioactive decay within an environment of the portable X-ray fluorescence analyzer and or ionizing radiation that propagates past a front end of the portable X-ray fluorescence analyzer towards its user.

13 Claims, 2 Drawing Sheets

X-RAY FLUORESCENCE ANALYZER WITH SAFETY FEATURES

TECHNICAL FIELD

The invention concerns in general the technical field of using X-ray fluorescence analysis for examining unknown samples. Especially the invention concerns means for making the use of such device in a potentially hazardous environment safer to its user.

BACKGROUND OF THE INVENTION

Handheld or otherwise portable X-ray fluorescence analyzers, or XRF analyzers for short, are frequently used in places like scrapyards, dumping grounds, and recycling centers to recognize and sort objects according to the useful materials they contain. An XRF analyzer comprises an initial radiation source, which is typically a small X-ray tube. The initial radiation is directed to the object to be examined or sample, where it causes the emission of fluorescent X-rays at the characteristic energies of the constituents of the sample. The XRF analyzer comprises also a detector, which receives fluorescent X-rays and measures their energy spectrum. The relative intensities of characteristic peaks in the measured energy spectrum reveal the element constitution of the sample.

The designer of the analyzer takes all possible precautions to ensure that X-rays generated in the measurement, i.e. the initial radiation and the fluorescent X-rays generated in the sample, will not constitute a hazard to the user. With appropriate structural solutions the designer tries to ensure that incident radiation is only directed towards the sample, and that fluorescent X-rays are only generated in a limited portion of the sample from which they cannot reach the user. A variety of structural and functional solutions may be used in the front end of the XRF analyzer to ensure that the emission of incident radiation is only possible when the analyzer has been pressed against the solid surface of a sample. Known measures include shutter arrangements in the front end window and/or at the exit aperture of the X-ray tube, as well as mechanical and/or optical proximity sensors that only allow the X-ray tube to be energized when the front end is against a sample.

In some cases the use of an additional radiation shield is recommended. Some sample materials are more prone than others to causing backscattering of incident radiation, and some materials encountered in samples give rise to exceptionally high levels of fluorescent X-rays. The use of an additional shield is typically recommended in analyzing materials of low density and/or powdery samples. However, the user may experience the additional radiation shield as bulky and uncomfortable.

Also unknown radiation hazards may be encountered when using a portable XRF analyzer. Since it is not known what is in there among the objects to be analyzed, little can be said beforehand about the environment of the measurement posing or not posing a hazard to the user. There is a clear need for solutions that could protect the user of the portable XRF analyzer from hazardous aspects that may occur in the environment in which the analyzer is used.

SUMMARY OF THE INVENTION

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

According to an aspect of the invention there is provided a portable XRF analyzer that enhances the personal safety of its user. According to another aspect of the invention there is provided a portable XRF analyzer that helps to detect and localize hazards in a measurement environment. According to yet another aspect of the invention there is provided a portable XRF analyzer that includes a synergetic combination of measurement methods.

Advantageous objectives of the invention are achieved by using a detector of ionizing radiation in a portable XRF analyzer. A signal from the detector may be used to trigger an alarm that indicates hazardous ionizing radiation within an area in which the user is or which the user is about to enter. Additionally or alternatively the signal from the detector may be used to prevent the emission of incident radiation from the XRF analyzer, thus precluding the user from making measurements in a hazardous environment or measurements of samples that may give rise to exceptionally high backscattering and/or fluorescence.

The detector of ionizing radiation should be operative constantly or regularly, and it may enable detecting the environmental hazard already before the user begins an actual X-ray fluorescence analysis. It is advantageous to place the detector of ionizing radiation at or near the outer cover of the portable XRF analyzer. Further it may be placed at a location in which it detects at least such ionizing radiation that is directed towards the hand or other body part that holds the portable XRF analyzer.

The portable XRF analyzer may comprise one, two, or more detectors of ionizing radiation. For example, there may be detectors that are sensitive to different kinds of ionizing radiation, and/or sensitive to ionizing radiation at different energies. There may be some directional sensitivity inherent to at least one detector of ionizing radiation, so that it becomes possible to localize the most prominent radiation hazard by pointing the portable XRF analyzer to different directions.

The exemplary embodiments of the invention presented in this patent application are not to be interpreted to pose limitations to the applicability of the appended claims. The verb "to comprise" is used in this patent application as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF EMBODIMENTS OF THE INVENTION

Some radiation hazards that the user of a portable XRF analyzer may encounter come from radioactive materials that may appear among the samples to be measured. The general concept "radioactive materials" covers all materials containing elements that are likely to undergo spontaneous radioactive decay, causing the emission of ionizing radiation. The common kinds of ionizing radiation are alpha, beta, and gamma radiation. All of these are hazardous to biological organisms, but due to the moderate propagation distances of alpha and beta particles in air, and also due to their strong attenuation in even relatively thin layers of solid material, gamma radiation or gamma rays are probably the most important kind of ionizing radiation against which the user of a portable XRF analyzer should be protected under normal operating conditions.

Figure 1:
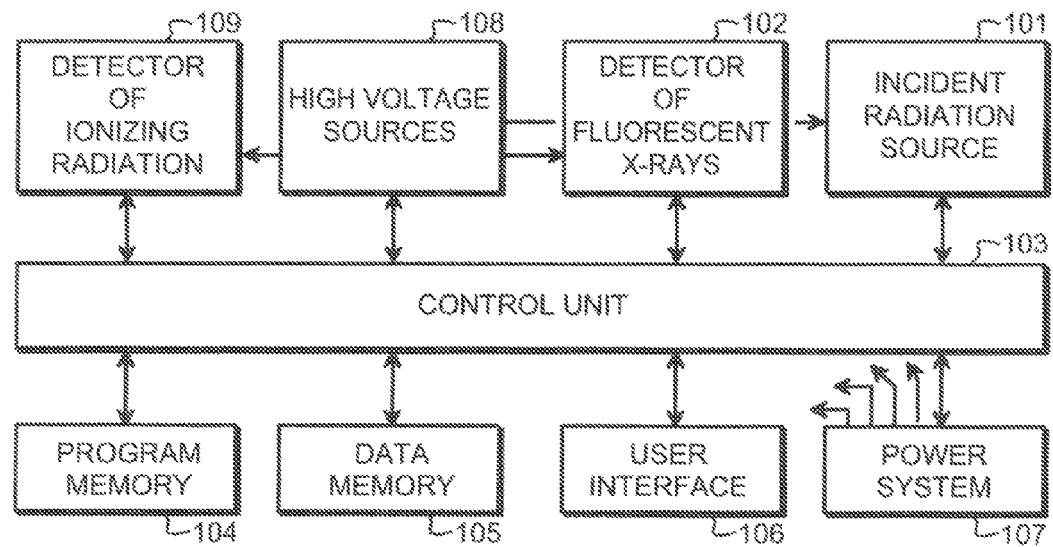
FIG. 1 illustrates some functionalities of a portable XRF analyzer.

FIG. 1 illustrates some functionalities of a portable XRF analyzer according to an embodiment of the invention. The XRF analyzer comprises an incident radiation source 101, which is typically a small-sized X-ray tube. It comprises also a detector of fluorescent X-rays 102, which may be for example a PIN detector or a SDD (silicon drift detector). These can be enabled and disabled by, and operate also otherwise under the supervision of, a control unit 103, which comprises a microprocessor. The operation of the control unit is determined by computer program products that are stored on a non-volatile computer readable medium, represented as a program memory 104 in FIG. 1. The computer program products comprise computer-readable instructions that, when executed by the microprocessor comprised in the control unit 103, cause the implementation of those methods that the XRF analyzer should perform. Collected data, reference data, and the like are stored in a data memory 105, and communications with a user take place through a user interface 106. A power source 107 stores and distributes electric power to other functional blocks, and one or more high voltage sources 108 generate the high voltages that are needed in the incident radiation source 101 and the detector of fluorescent X-rays 102.

The portable XRF analyzer of FIG. 1 comprises a detector of ionizing radiation 109 that is configured to detect radiation from spontaneous radioactive decay within an environment of the portable XRF analyzer. Additionally or alternatively the detector of ionizing radiation 109 may be configured to detect ionizing radiation propagating past a front end of the portable X-ray fluorescence analyzer towards its user; in particular, backscattered incident radiation and/or fluorescent X-rays generated in the sample. The type of detector to be used may be selected according to what kind of ionizing radiation would be considered most important to detect in the operating environment of the XRF analyzer. For example, the detector of ionizing radiation 109 may be a solid-state semiconductor detector optimized to detect gamma rays that radioactive nuclei emit. If it needs high voltages for biasing, these can be taken from the high voltage sources that are already included in block 108 for powering the incident radiation source 101 and the detector 102, or from a separate, dedicated high voltage source.

When the detector of ionizing radiation 109 detects radiation that—judging by its kind and energy level—is likely to have originated from spontaneous radioactive decay within an environment of the portable X-ray fluorescence analyzer, it outputs a signal to the control unit 103. Similarly a signal is output if the detector of ionizing radiation 109 detects ionizing radiation that propagates past the front end towards the user. The desired response of the control unit can be determined by providing corresponding computer-readable instructions in the program that is stored in the program memory 104. For example, the control unit 103 may be configured to provide an indication through the user interface 106 as a response to a signal from the detector of ionizing radiation 109 that indicates presence of radiation from spontaneous radioactive decay. The indication may comprise for example an audible warning, and/or a message displayed on a display, and/or the illumination of a warning lamp or other visual indicator. This way the user gets a warning and may take appropriate action, like leaving the area and/or putting on protective gear.

The control unit 103 may also be configured to respond to said signal from the detector of ionizing radiation 109 by disabling the incident radiation source 101. Although the incident radiation from an XRF analyzer is not likely to have any effect on the spontaneous radioactive decay of radionuclides, it may nevertheless by preferable not to deliberately produce additional ionizing radiation when an uncontrolled radiation source has been detected. Disabling the incident radiation source 101 is also justified if the detector of ionizing radiation 109 detected backscattered incident radiation and/or ionizing radiation that propagates past the front end towards the user.

The user interface 106 should preferably offer an override possibility through which the user may command re-enabling the incident radiation source 101 in case a somewhat radioactive sample should be subjected to XRF analysis, or XRF analysis should otherwise be performed in an environment that is known to contain some ionizing radiation or cause a large amount of backscattering or fluorescent X-rays.

Saying that the detector of ionizing radiation 109 detects radiation from spontaneous radioactive decay within an environment of the portable X-ray fluorescence analyzer and outputs a signal, and that the control unit 103 responds in a desired way, contains an implicit assumption of some kind of a threshold level. Small but detectable amounts of ionizing radiation occur naturally all the time, originating from for example cosmic rays and naturally existing radionuclides with very low concentrations and/or very long half-lives. The threshold level applied in the detection of ionizing radiation should be such that only radioactivity that is above the naturally occurring background is reacted upon. The same applies to backscattered incident radiation and other potentially hazardous radiation: only meaningful amounts should be reacted to.

Figure 2:
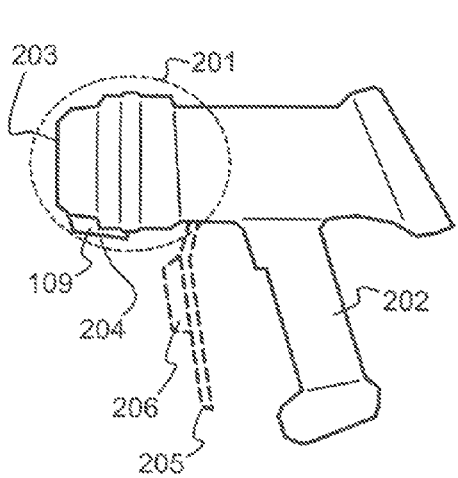
FIG. 2 illustrates possible locations of a detector of ionizing radiation in a portable XRF analyzer.

FIG. 2 illustrates schematically a portable XRF analyzer seen from the side. The portion inside the dashed oval could be designated as a front part 201, because this is the part of the device that will be directed towards a sample to be analyzed. The front part 201 houses the incident radiation source and the detector of fluorescent X-rays. In the embodiment illustrated in FIG. 2 also the detector of ionizing radiation 109 is located in the front part 201. This kind of location of the detector of ionizing radiation 109 may have particular significance if the kind and/or energy and/or intensity of ionizing radiation to be primarily detected are such that its detectable range in ambient air is not very long. When the detector of ionizing radiation 109 is located in a part of the analyzer that will be placed close to a sample in normal use, the attenuation of ionizing radiation in ambient air before detection as well as the geometric decrease in flux (which is proportional to the square of the distance) can be minimized.

The location of the detector of ionizing radiation 109 in the front part 201 has also other advantages. It is the front part 201 in which also other radiation-related components are located, so for example the internal electric connections for high voltages remain short.

The portable XRF analyzer of FIG. 2 comprises a handle 202 for holding the portable XRF analyzer. In normal use the user will grab the handle 202 with one hand, with the front part 201 pointing directly away from the user. The distant end of the front part 201 is the front end 203, which defines for example a measurement aperture (not shown in FIG. 2) for fluorescent X-rays. An advantageous location for the detector of ionizing radiation 109 can also be defined so that it is located between the front end 203 and the handle 202. This way it can be ensured that if the potentially hazardous ionizing radiation originates from approximately the same region at which the user intends to point the portable XRF analyzer for measuring, an indication will be received of that portion of the ionizing radiation that would become directed to those parts of the user that are closest to the source of the ionizing radiation.

In the embodiment illustrated with solid lines in FIG. 2 the location selected for the detector of ionizing radiation 109 according to the principles outlined above is in the front part 201, under the "snout" or forward protruding part (in the normal operating position) of the portable XRF analyzer, protected by an outer cover part 204 that may be integral with the outer cover of the portable XRF analyzer or attached thereto. An alternative solution is illustrated in FIG. 2 with dashed lines. According to the alternative embodiment the portable XRF analyzer comprises a shield 205 on that side of the handle 202 that is directed to the same direction as the front end 203, and the detector of ionizing radiation 206 is located in the shield 205. The shield 205 may be simply a mechanical shield that protects the hand of the user against bruises, or it may be a heat shield or a radiation shield.

Figure 3:
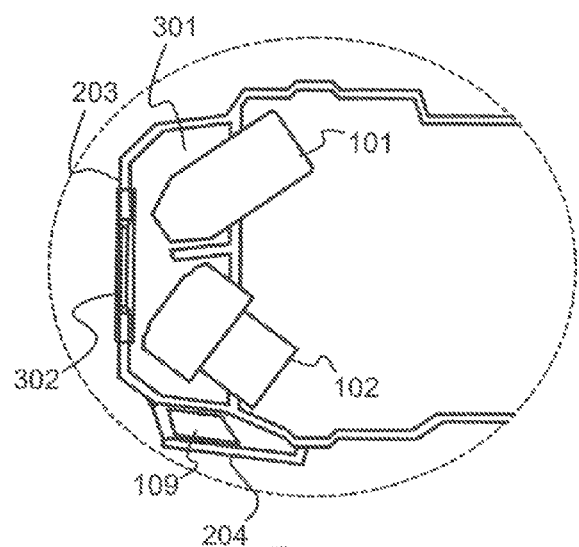
FIG. 3 illustrates the concepts of a shutter and a measurement chamber.

FIG. 3 is a schematic partial cutout illustration of a front part of a portable XRF analyzer. The front part houses an incident radiation source 101 and a detector of fluorescent X-rays 102. The front part also houses a measurement chamber 301, which is an essentially closed space within which the radiation emitting surface of the incident radiation source 101 and the radiation receiving surface of the detector of fluorescent X-rays 102 are located. The front end 203 of the XRF analyzer defines a measurement aperture, through which incident radiation from the incident radiation source 101 may reach the sample and through which the fluorescent X-rays from the sample may reach the detector of fluorescent X-rays 102. A shutter 302 may appear at the measurement aperture and have an open position and a closed position, in which closed position the shutter 302 closes an access of X-rays to the measurement chamber 301 through the measurement aperture.

Basically, if the dynamic range and other characteristics are suitable, it would be possible to use the detector of fluorescent X-rays 102 also as the detector of ionizing radiation mentioned above, for example in alternating turns so that the same device would function as the detector of ionizing radiation whenever it is not operational as the detector of fluorescent X-rays. However, in many cases it is more advantageous that the detector of ionizing radiation 109 is separate from the detector of fluorescent X-rays 102 comprised in the portable XRF analyzer, even so that the detector of ionizing radiation 109 is located outside the measurement chamber 301.

Figure 4:
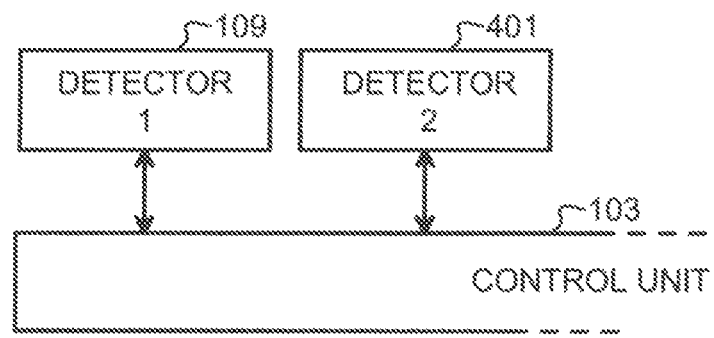
FIG. 4 illustrates the principle of having two or more detectors of ionizing radiation.

If a shutter 302 is present, In its closed position the shutter 302 may significantly attenuate at least some of the softer end of radiation from spontaneous radioactive decay within an environment of the portable XRF analyzer, which means that any detector, the radiation receiving surface of which is located in the measurement chamber 301, is not as sensitive when the shutter 302 is in its closed position. Also since detectors and their associate amplifiers and other pre-processing circuitry are typically optimized for a particular kind and energy range of radiation, it may be better to have two separate detectors, one for fluorescent X-rays and the other for ionizing radiation from spontaneous radioactive decay within an environment of the portable XRF analyzer. Due to its position within the measurement chamber and immediately behind the front end of the portable XRF analyzer, the detector of fluorescent X-rays 102 is also ill suited for detecting ionizing radiation that propagates past a front end of the portable X-ray fluorescence analyzer towards its user FIG. 4 illustrates schematically the possibility that the portable XRF analyzer may comprise two or more different detectors of ionizing radiation. At least one of the first 109 and the second 401 detector of ionizing radiation are configured to detect radiation from spontaneous radioactive decay within an environment of the portable XRF analyzer. However, the two (or at least two of those different detectors of ionizing radiation that are included in the analyzer) differ from each other in being sensitive to different kinds of ionizing radiation, and/or to ionizing radiation at different energies. For example, if the first 109 detector is sensitive to gamma rays, the second 401 detector may be a detector of beta particles.

Figure 5:
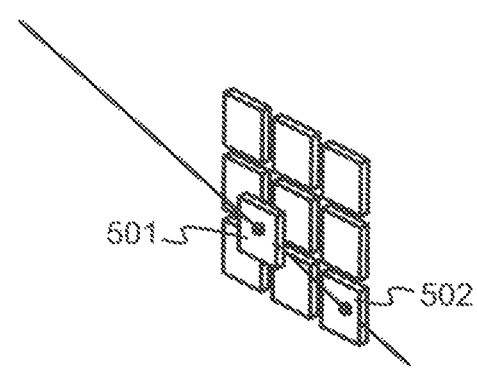
FIG. 5 illustrates an example of a detector that is sensitive to the propagation direction of the ionizing radiation.

The use of a portable XRF analyzer for detecting radiation from spontaneous radioactive decay within an environment of the portable XRF analyzer becomes even more versatile if at least one detector of ionizing radiation comprised by the portable XRF analyzer is sensitive to the propagating direction of ionizing radiation. FIG. 5 illustrates schematically the operating principle of a simple direction-sensitive detector. The detector comprises two concatenated pixel matrices. In the example of FIG. 5 the front matrix is small and may comprise even a single pixel 501, while the back matrix is wider and comprises a number of pixels, of which the lower right pixel 502 is shown as an example. When the geometric relations are known, and coincidence detection can be made between the two concatenated pixel matrices, the direction from which each gamma ray was received can be calculated.

With at least one direction-sensitive detector at its disposal, the control unit may be configured to provide changing intensity indications of detected ionizing radiation through the user interface as a response to changes in the orientation of the portable XRF analyzer in relation to the propagating direction of ionizing radiation. In other words, the user could find out, by pointing the portable XRF analyzer to different directions, in which direction the source of ionizing radiation is located. This could help the user to minimize the radiation hazards to which he or she will be exposed.

A method that the processor of the portable XRF analyzer may perform according to an embodiment of the invention may comprise measuring an amount of ionizing radiation from spontaneous radioactive decay within an environment of the portable X-ray fluorescence analyzer, and—as a response to a measurement that shows the intensity of ionizing radiation from spontaneous radioactive decay to exceed a predetermined threshold—producing an indication. Additionally or alternatively the method may comprise measuring an amount of ionizing radiation that propagates past a front end of the portable X-ray fluorescence analyzer towards its user, and reacting to measurement result as explained above.

The method may also comprise providing, through a user interface of the portable X-ray fluorescence analyzer, an indication of detected ionizing radiation, and/or disabling an incident radiation source comprised in the portable X-ray fluorescence analyzer.

Variations and modifications are possible to the embodiments described above without parting from the scope of protection defined by the appended claims. For example, even if the discussion earlier has mainly suggested using the detector of ionizing radiation to detect the mere presence of potentially harmful ionizing radiation, it may also be used to reveal the overall intensity and/or some characteristics of the energy spectrum of the detected ionizing radiation, if the detector and the associated processing electronics are capable of energy dispersive operation. If for example a prominent energy of detected gamma rays could be announced, the user could utilize it to conclude, from which radioactive isotope the detected radiation comes from. If at least the approximate intensity of the detected radiation could be announced, the user could utilize it to evaluate, how severe is the detected radiation hazard. Yet another class of variations comes from using a dosimeter as a detector of ionizing radiation, so instead of or in addition to real-time detection of radiation, the user could obtain an indication of the overall radiation dose that he or she has been exposed to. A dosimeter could be located for example inside the handle of the portable XRF analyzer, in which case it could give relatively reliable indications of the radiation dose absorbed by the hand of the user.

What is claimed is:

1. A portable X-ray fluorescence analyzer, comprising a control unit and a detector of ionizing radiation, wherein:
    the detector of ionizing radiation is configured to detect at least one of:
        radiation from spontaneous radioactive decay within an environment of the portable X-ray fluorescence analyzer, and
        ionizing radiation propagating past a front end of the portable X-ray fluorescence analyzer towards its user;
    and the control unit is arranged to enable and disable an incident radiation source of portable X-ray fluorescence analyzer and is configured to disable said incident radiation source in remorse to a signal from the detector of ionizing radiation indicating presence of at least one of:
        radiation from spontaneous radioactive decay, and
        ionizing radiation propagating past the front end of the portable X-ray fluorescence analyzer towards its user.

2. A portable X-ray fluorescence analyzer according to claim 1, comprising a front part that houses the incident radiation source and a detector of fluorescent X-rays, wherein the detector of ionizing radiation is located in said front part.

3. A portable X-ray fluorescence analyzer according to claim 1, wherein:
    the front end defines a measurement aperture for fluorescent X-rays,
    the portable X-ray fluorescence analyzer comprises a handle for holding the portable X-ray fluorescence analyzer, and
    the detector of ionizing radiation is located between said front end and said handle.

4. A portable X-ray fluorescence analyzer according to claim 3, comprising a shield on that side of said handle that is directed to the same direction as said front end, wherein the detector of ionizing radiation is located in the shield.

5. A portable X-ray fluorescence analyzer according to claim 1, wherein said detector of ionizing radiation is separate from a detector of fluorescent X-rays comprised in said portable X-ray fluorescence analyzer.

6. A portable X-ray fluorescence analyzer according to claim 1, comprising:
    a detector of fluorescent X-rays, having a radiation receiving surface within a measurement chamber accessed through an aperture in said front end;
wherein said detector of ionizing radiation is located outside said measurement chamber.

7. A portable X-ray fluorescence analyzer according to claim 1, further comprising a user interface, wherein said control unit is configured to provide an indication through said user interface as a response to said signal from the detector of ionizing radiation.

8. A portable X-ray fluorescence analyzer according to claim 1, comprising two or more detectors of ionizing radiation, each of which is configured to detect radiation from at least one of: spontaneous radioactive decay within an environment of the portable X-ray fluorescence analyzer and ionizing radiation propagating past the front end of the portable X-ray fluorescence analyzer.

9. A portable X-ray fluorescence analyzer according to claim 8, wherein at least two of said two or more detectors differ from each other in being sensitive to at least one of: different kinds of ionizing radiation, and ionizing radiation at different energies.

10. A portable X-ray fluorescence analyzer according to claim 1, wherein at least one detector of ionizing radiation comprised by the portable X-ray fluorescence analyzer is sensitive to the propagating direction of ionizing radiation.

11. A portable X-ray fluorescence analyzer according to claim 10, further comprising a user interface, of which said control unit is configured to provide changing intensity indications of detected ionizing radiation through said user interface as a response to changes in the orientation of the portable X-ray fluorescence analyzer in relation to the propagating direction of ionizing radiation.

12. A computer program product stored on a non-volatile computer readable medium, comprising computer-readable instructions that, when executed by a processor comprised in a portable X-ray fluorescence analyzer, cause the implementation of a method comprising:
    measuring at least one of: an amount of ionizing radiation from spontaneous radioactive decay within an environment of the portable X-ray fluorescence analyzer, and ionizing radiation propagating past a front end of the portable X-ray fluorescence analyzer towards its user, and
    as a response to said measuring, providing a signal that results ire disabling of an incident radiation source of the portable X-ray fluorescence analyzer.

13. A computer program product according to claim 12, wherein as a response to a measurement that shows the intensity of ionizing radiation from spontaneous radioactive decay to exceed a predetermined threshold,
    providing, through a user interface of the portable X-ray fluorescence analyzer, an indication of detected ionizing radiation.

* * * * *

UNITED STATES PATENT AND TRADEMARK OFFICE
CERTIFICATE OF CORRECTION

| | | |
|---|---|---|
| PATENT NO. | : 9,310,324 B2 | Page 1 of 1 |
| APPLICATION NO. | : 14/034607 | |
| DATED | : April 12, 2016 | |
| INVENTOR(S) | : Mikko Järvikivi et al. | |

It is certified that error appears in the above-identified patent and that said Letters Patent is hereby corrected as shown below:

In the Claims

In Claim 1:
Column 7, line 40, "of portable" should be deleted and --of the portable-- should be inserted.

Column 7, line 42, "remorse" should be deleted and --response-- should be inserted.

In Claim 12:
Column 8, line 54, "ire" should be deleted and --in-- should be inserted.

Signed and Sealed this
Twenty-eighth Day of June, 2016

Michelle K. Lee
*Director of the United States Patent and Trademark Office*